US008252806B2

(12) United States Patent
Eriksen et al.

(10) Patent No.: US 8,252,806 B2
(45) Date of Patent: Aug. 28, 2012

(54) POTASSIUM CHANNEL MODULATING AGENTS AND THEIR MEDICAL USE

(75) Inventors: Birgitte L. Eriksen, Farum (DK); Lene Teuber, Værløse (DK); Charlotte Hougaard, Bagsværd (DK); Ulrik Svane Sørensen, Søborg (DK)

(73) Assignee: Neurosearch A/S, Ballerup (DK)

( * ) Notice: Subject to any disclaimer, the term of this patent is extended or adjusted under 35 U.S.C. 154(b) by 1328 days.

(21) Appl. No.: 11/886,341

(22) PCT Filed: Mar. 13, 2006

(86) PCT No.: PCT/EP2006/060643
§ 371 (c)(1),
(2), (4) Date: Oct. 2, 2007

(87) PCT Pub. No.: WO2006/097441
PCT Pub. Date: Sep. 21, 2006

(65) Prior Publication Data
US 2008/0275045 A1 Nov. 6, 2008

Related U.S. Application Data

(60) Provisional application No. 60/661,149, filed on Mar. 14, 2005.

(30) Foreign Application Priority Data

Mar. 14, 2005 (DK) ................ 2005 00366

(51) Int. Cl.
*A01N 43/54* (2006.01)
*A61K 31/517* (2006.01)
*C07D 401/00* (2006.01)
(52) U.S. Cl. .................. 514/266.23; 544/284
(58) Field of Classification Search ............. 514/266.23; 544/284
See application file for complete search history.

(56) References Cited

U.S. PATENT DOCUMENTS

| 5,439,895 A | 8/1995 | Lee et al. |
| 5,576,322 A | 11/1996 | Takase et al. |
| 6,476,031 B1 | 11/2002 | Chakravarty et al. |
| 7,678,802 B2 * | 3/2010 | Gonzalez et al. .......... 514/266.2 |
| 2009/0036475 A1 | 2/2009 | Eriksen et al. |

FOREIGN PATENT DOCUMENTS

| EP | 0 579 496 A | 1/1994 |
| EP | 0 607 439 A | 7/1994 |
| JP | 6-192235 A | 7/1994 |
| JP | 10095776 A | 4/1998 |
| JP | 2004-524350 A | 8/2004 |
| JP | 2006-522119 A | 9/2006 |
| WO | WO-89/05297 A1 | 6/1989 |
| WO | 02076976 A2 | 10/2002 |
| WO | 2004078733 A1 | 9/2004 |
| WO | WO-2006/071095 A1 | 7/2006 |

OTHER PUBLICATIONS

Faber, L ES et. al., "Functions of SK Channels in Central Neurons", Clinical and Experimental Pharmacology and Physiology, (2007), vol. 34, pp. 1077-1083.*
Sobey, C.G., "Potassium Channel Function in Vascular Disease", Arteriosclerosis, Thrombosis, and Vascular Biology, (2001), © by American Heart Association, Inc., pp. 28-38.*
A. Kamal, et al., Indian Journal of Chemistry, vol. 24B, Apr. 1985, pp. 414-418.

* cited by examiner

*Primary Examiner* — Paul V. Ward
(74) *Attorney, Agent, or Firm* — Birch, Stewart, Kolasch & Birch, LLP

(57) ABSTRACT

This invention relates to novel potassium channel modulating agents, and their use in the preparation of pharmaceutical compositions.

Moreover the invention is directed to pharmaceutical compositions useful for the treatment or alleviation of diseases or disorders associated with the activity of potassium channels, in particular respiratory diseases, epilepsy, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, schizophrenia, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, immune suppression or pain.

15 Claims, No Drawings

POTASSIUM CHANNEL MODULATING AGENTS AND THEIR MEDICAL USE

This application is the national phase of PCT application PCT/EP2006/060643 filed on Mar. 13, 2006 and claims priority under 35 U.S.C. 119(e) on Provisional Application No(s). 60/661,149 filed on Mar. 14, 2005 and under 35 U.S.C. 119(a) on patent application No(s). PA 2005 00366 filed in Denmark on Mar. 14, 2005, all of which are hereby incorporated by reference.

TECHNICAL FIELD

This invention relates to novel potassium channel modulating agents, and their use in the preparation of pharmaceutical compositions.

Moreover the invention is directed to pharmaceutical compositions useful for the treatment or alleviation of diseases or disorders associated with the activity of potassium channels, in particular respiratory diseases, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, ataxia, traumatic brain injury, Parkinson's disease, bipolar disorder, psychosis, schizophrenia, anxiety, depression, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine or pain.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_V$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer and immune suppression.

SUMMARY OF THE INVENTION

The present invention resides in the provision of novel chemical compounds capable of selectively modulating SK channels, or subtypes of SK channels.

Moreover the invention is directed to pharmaceutical compositions useful for the treatment or alleviation of diseases or disorders associated with the activity of potassium channels, including diseases or conditions like respiratory diseases, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, ataxia, traumatic brain injury, Parkinson's disease, bipolar disorder, psychosis, schizophrenia, anxiety, depression, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine or pain.

Accordingly, in its first aspect, the invention provides novel pyrazolyl-quinazoline derivatives of Formula I

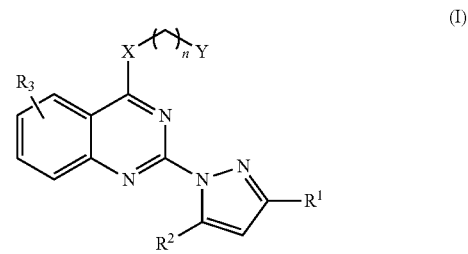

(I)

an isomer or a mixture of its isomers, an N-oxide thereof, or a pharmaceutically acceptable salt thereof, wherein n is 0, 1, 2 or 3;

X represents O, S or NR'; wherein

R' represents hydrogen, alkyl, cycloalkyl or cycloalkyl-alkyl;

or, when n is 0 and X is NR', R' together with Y and together with the nitrogen to which they are attached form a heterocyclic ring, which heterocyclic ring may optionally be substituted with alkyl or phenyl;

Y represents alkyl, amino-alkyl, alkyl-amino, alkyl-amino-alkyl, hydroxy-alkyl, alkoxy-alkyl, alkenyl, or a monocyclic or polycyclic, carbocyclic, or heterocyclic group, which carbocyclic or heterocyclic groups may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro, amino, methylenedioxy, phenyl and morpholinyl;

or, when n is 0 and X is NR', Y together with R' and together with the nitrogen to which they are attached form a heterocyclic ring, which heterocyclic ring may optionally be substituted with alkyl or phenyl; and $R^1$, $R^2$ and $R^3$ independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In another aspect, the invention provides pharmaceutical compositions comprising an effective amount of a chemical compound of the invention.

In further aspects the invention relates to the use of a chemical compound of the invention for the manufacture of a medicament for the treatment or alleviation of diseases or disorders associated with the activity of potassium channels, and to method of treatment or alleviation of disorders or conditions responsive to modulation of potassium channels.

DETAILED DISCLOSURE OF THE INVENTION

Potassium Channel Modulating Agents

In its first aspect, the invention provides novel pyrazolyl-quinazoline derivatives represented by Formula I

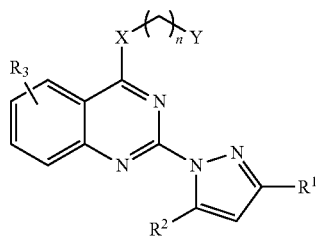

(I)

an isomer or a mixture of its isomers, an N-oxide thereof, or a pharmaceutically acceptable salt thereof, wherein n is 0, 1, 2 or 3;

X represents O, S or NR'; wherein

R' represents hydrogen, alkyl, cycloalkyl or cycloalkyl-alkyl;

or, when n is 0 and X is NR', R' together with Y and together with the nitrogen to which they are attached form a heterocyclic ring, which heterocyclic ring may optionally be substituted with alkyl or phenyl;

Y represents alkyl, amino-alkyl, alkyl-amino, alkyl-amino-alkyl, hydroxy-alkyl, alkoxy-alkyl, alkenyl, or a monocyclic or polycyclic, carbocyclic, or heterocyclic group, which carbocyclic or heterocyclic groups may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro, amino, methylenedioxy, phenyl and morpholinyl;

or, when n is 0 and X is NR', Y together with R' and together with the nitrogen to which they are attached form a heterocyclic ring, which heterocyclic ring may optionally be substituted with alkyl or phenyl; and $R^1$, $R^2$ and $R^3$ independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a preferred embodiment pyrazolyl-quinazoline derivative of the invention is a compound of Formula I wherein n is 0, 1, 2 or 3.

In a more preferred embodiment n is 0, 1 or 2.

In an even more preferred embodiment n is 0 or 1.

In a most preferred embodiment n is 0.

In another preferred embodiment the pyrazolyl-quinazoline derivative of the invention is a compound of Formula I wherein X represents O, S or NR'; wherein R' represents hydrogen, alkyl, cycloalkyl or cycloalkyl-alkyl; or, when n is 0 and X is NR', R' together with Y and together with the nitrogen to which they are attached form a heterocyclic ring, which heterocyclic ring may optionally be substituted with alkyl or phenyl.

In a more preferred embodiment X represents NR'; wherein R' represents hydrogen, alkyl, cycloalkyl or cycloalkyl-alkyl.

In an even more preferred embodiment X represents NR'; wherein R' represents hydrogen or alkyl.

In a still more preferred embodiment X represents NR'; wherein R' represents hydrogen, methyl, ethyl or propyl.

In a yet more preferred embodiment X represents NH.

In another preferred embodiment n is 0; X represents NR'; and R' together with Y and together with the nitrogen to which they are attached form a heterocyclic ring, which heterocyclic ring may optionally be substituted with alkyl or phenyl.

In a more preferred embodiment n is 0; X represents NR'; and R' together with Y and together with the nitrogen to which they are attached form a pyrrolidinyl, piperidinyl, piperazinyl or morpholinyl ring.

In an even more preferred embodiment n is 0; X represents NR'; and R' together with Y and together with the nitrogen to which they are attached form a piperidinyl ring.

In a third preferred embodiment the pyrazolyl-quinazoline derivative of the invention is a compound of Formula I wherein Y represents alkyl, amino-alkyl, alkyl-amino, alkyl-amino-alkyl, hydroxy-alkyl, alkoxy-alkyl, alkenyl, or a monocyclic or polycyclic, carbocyclic or heterocyclic group, which carbocyclic or heterocyclic groups may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro, amino, methylenedioxy, phenyl and morpholinyl; or, when n is 0 and X is NR', Y together with R' and together with the nitrogen to which they are attached form a heterocyclic ring, which heterocyclic ring may optionally be substituted with alkyl or phenyl.

In a more preferred embodiment Y represents alkyl, alkenyl, or cycloalkyl.

In an even more preferred embodiment Y represents methyl, ethyl, propyl, butyl, pentyl allyl, cyclopropyl, cyclopentyl, cyclohexyl, cycloheptyl or cyclooctyl.

In a still more preferred embodiment Y represents ethyl, allyl, cyclopropyl, cyclopentyl, cyclohexyl or cyclooctyl.

In a yet more preferred embodiment Y represents cycloalkyl, optionally substituted with alkyl.

In a yet further preferred embodiment Y represents cyclopropyl, cyclopentyl, cyclohexyl, cycloheptyl or cyclooctyl, optionally substituted with alkyl.

In a still further preferred embodiment Y represents cyclopropyl, cyclopentyl, cyclohexyl, cycloheptyl or cyclooctyl, optionally substituted with methyl or tert-butyl.

In a still further preferred embodiment Y represents cyclohexyl substituted with alkyl.

In a still further preferred embodiment Y represents cyclohexyl substituted with methyl or tert-butyl.

In another preferred embodiment Y represents a monocyclic or polycyclic carbocyclic group selected from phenyl, naphthyl or 1,2,3,4-tetrahydro-naphthyl; or a monocyclic or polycyclic heterocyclic group selected from pyrrolidinyl, piperidinyl, furanyl, thienyl and pyrrolyl; which phenyl, naphthyl, 1,2,3,4-tetrahydro-naphthyl, pyrrolidinyl, piperidinyl, furanyl, thienyl and pyrrolyl groups may optionally be substituted one or two times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino.

In a more preferred embodiment Y represents phenyl, naphthyl, 1,2,3,4-tetrahydro-naphthyl, pyrrolidinyl, piperidinyl, furanyl, thienyl or pyrrolyl; which phenyl, naphthyl, 1,2,3,4-tetrahydro-naphthyl, pyrrolidinyl, piperidinyl, furanyl, thienyl and pyrrolyl groups may optionally be substituted one or two times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino.

In an even more preferred embodiment Y represents phenyl, naphth-1-yl, naphth-2-yl, 1,2,3,4-tetrahydro-naphth-1-yl, 1,2,3,4-tetrahydro-naphth-2-yl, pyrrolidin-1-yl, piperidin-1-yl, piperidin-4-yl, furan-2-yl, furan-3-yl, thien-1-yl, thien-2-yl, pyrrol-1-yl or pyrrol-2-yl; which phenyl, naphthyl, 1,2,3,4-tetrahydro-naphthyl, pyrrolidinyl, piperidinyl, furanyl, thienyl and pyrrolyl groups may optionally be substituted one or two times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro and amino.

In a still more preferred embodiment the phenyl, naphthyl, 1,2,3,4-tetrahydro-naphthyl, pyrrolidinyl, piperidinyl, furanyl, thienyl and pyrrolyl groups may optionally be substituted one or two times with substituents selected from the group consisting of alkyl, halo, haloalkyl, alkoxy.

In a yet more preferred embodiment the phenyl, naphthyl, 1,2,3,4-tetrahydro-naphthyl, pyrrolidinyl, piperidinyl, furanyl, thienyl and pyrrolyl groups may optionally be substituted one or two times with substituents selected from the group consisting of methyl, ethyl, propyl, chloro, fluoro, bromo, trifluoromethyl, methoxy or ethoxy.

In a further preferred embodiment Y represents a monocyclic or polycyclic carbocyclic group selected from phenyl, naphthyl, 1,2,3,4-tetrahydro-naphthyl and indanyl, which carbocyclic groups may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro, amino, methylenedioxy, phenyl and morpholinyl.

In a still further preferred embodiment Y represents phenyl, naphthyl, 1,2,3,4-tetrahydro-naphthyl and indanyl, which carbocyclic groups may optionally be substituted one or two times with substituents selected from the group consisting of alkyl, halo, haloalkyl, alkoxy, methylenedioxy, phenyl and morpholinyl.

In a still further preferred embodiment Y represents phenyl, naphthyl, 1,2,3,4-tetrahydro-naphthyl and indanyl, which carbocyclic groups may optionally be substituted one or two times with substituents selected from the group consisting of methyl, tert-butyl, fluoro, chloro, bromo, iodo, trifluoromethyl, methoxy, methylenedioxy, phenyl and morpholinyl.

In a still further preferred embodiment Y represents phenyl, optionally substituted one or two times with substituents selected from the group consisting of methyl, tert-butyl, fluoro, chloro, bromo, iodo, trifluoromethyl, methoxy, methylenedioxy, phenyl and morpholinyl.

In a still further preferred embodiment Y represents phenyl, optionally substituted with alkyl, halo, haloalkyl, alkoxy, methylenedioxy, phenyl or morpholinyl.

In a still further preferred embodiment Y represents phenyl, optionally substituted with methyl, tert-butyl, fluoro, chloro, bromo, iodo, trifluoromethyl, methoxy, methylenedioxy, phenyl or morpholinyl.

In a still further preferred embodiment Y represents a heterocyclic group, which carbocyclic or heterocyclic groups may optionally be substituted one or more times with substituents selected from the group consisting of alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, cyano, nitro, amino.

In a still further preferred embodiment Y represents tetrahydropyranyl, pyrrolidinyl, piperidinyl, furanyl, thienyl, pyrrolyl, pyridinyl, indolyl or quinolinyl.

In a most preferred embodiment Y represents tetrahydropyranyl, pyridinyl, indolyl or quinolinyl.

In a fourth preferred embodiment the pyrazolyl-quinazoline derivative of the invention is a compound of Formula I wherein $R^1$, $R^2$ and $R^3$ independently of each other, represent hydrogen, alkyl, amino-alkyl, alkyl-amino, alkyl-amino-alkyl, hydroxy-alkyl, alkoxy-alkyl, cycloalkyl, cycloalkyl-alkyl, alkenyl, halo, haloalkyl, hydroxy, alkoxy, haloalkoxy, alkoxy-carbonyl, cyano, nitro and amino.

In a fifth preferred embodiment the pyrazolyl-quinazoline derivative of the invention is a compound of Formula I wherein $R^1$, $R^2$ and $R^3$ independently of each other, represent hydrogen, alkyl, cycloalkyl, cycloalkyl-alkyl, alkenyl, halo, haloalkyl, hydroxy, alkoxy, haloalkoxy, alkoxy-carbonyl, cyano, nitro or amino.

In a more preferred embodiment $R^1$, $R^2$ and $R^3$, independently of each other, represent alkyl, cycloalkyl or cycloalkyl-alkyl.

In an even more preferred embodiment $R^1$, $R^2$ and $R^3$ independently of each other, represent hydrogen or alkyl.

In a still more preferred embodiment $R^1$, $R^2$ and $R^3$ independently of each other, represent methyl, ethyl or propyl.

In a yet more preferred embodiment $R^1$ and $R^2$ independently of each other, represent hydrogen or alkyl; and $R^3$ represents hydrogen.

In a further preferred embodiment $R^1$ and $R^2$ independently of each other, represent alkyl; and $R^3$ represents hydrogen.

In a still further preferred embodiment $R^1$ and $R^2$ represent methyl or isopropyl; and $R^3$ represents hydrogen.

In a still further preferred embodiment $R^1$ and $R^2$ represent methyl; and $R^3$ represents hydrogen.

In a still further preferred embodiment $R^1$ and $R^2$ represent isopropyl; and $R^3$ represents hydrogen.

In a still further preferred embodiment $R^1$ represents methyl; and $R^2$ and $R^3$ represent hydrogen.

In a still further preferred embodiment $R^1$, $R^2$ and $R^3$ represent hydrogen.

In a sixth preferred embodiment the pyrazolyl-quinazoline derivative of the invention is a compound of Formula I wherein n is 0; X represents O, S or NR'; wherein R' represents hydrogen, methyl, ethyl or propyl; Y represents alkyl, alkenyl, cycloalkyl, alkyl-cycloalkyl; $R^1$ and $R^2$ represent methyl or isopropyl; and $R^3$ represents hydrogen.

In a more preferred embodiment n is 0; X represents NH; Y represents alkyl, alkenyl, cycloalkyl, alkyl-cycloalkyl, naphthyl, 1,2,3,4-tetrahydro-naphthyl indanyl, tetrahydropyranyl, pyridinyl, indolyl or quinolinyl; $R^1$ and $R^2$ represent methyl or isopropyl; and $R^3$ represents hydrogen.

In a seventh preferred embodiment the pyrazolyl-quinazoline derivative of the invention is a compound of Formula I wherein n is 0; X represents NR'; wherein R' represents hydrogen, methyl, ethyl or propyl; Y represents alkyl (ethyl, propyl, butyl), cycloalkyl (cyclopropyl, cyclopentyl, cyclohexyl, cyclooctyl), cycloalkyl-alkyl, or alkenyl (allyl), piperidinyl or phenyl, which phenyl may optionally be substituted one or two times with halo or trifluoromethyl; and $R^1$, $R^2$ and $R^3$, independently of each other, represent methyl, ethyl or propyl.

In an eight preferred embodiment the pyrazolyl-quinazoline derivative of the invention is a compound of Formula I wherein n is 0 or 1; X represents NH; Y represents phenyl, optionally substituted one or two times with substituents selected from the group consisting of alkyl, halo, haloalkyl, alkoxy, methylenedioxy, phenyl and morpholinyl; $R^1$ and $R^2$ represent methyl or isopropyl; and $R^3$ represents hydrogen.

In a more preferred embodiment n is 0; X represents NH; Y represents phenyl, optionally substituted one or two times with substituents selected from the group consisting of alkyl, halo, haloalkyl, alkoxy, methylenedioxy, phenyl and morpholinyl; $R^1$ and $R^2$ represent methyl or isopropyl; and $R^3$ represents hydrogen.

In an even more preferred embodiment n is 1; X represents NH; Y represents phenyl, optionally substituted one or two times with substituents selected from the group consisting of alkyl, halo, haloalkyl, alkoxy, methylenedioxy, phenyl and morpholinyl; $R^1$ and $R^2$ represent methyl or isopropyl; and $R^3$ represents hydrogen.

In a still more preferred embodiment n is 1; X represents NH; Y represents phenyl, optionally substituted one or two times with substituents selected from the group consisting of halo or haloalkyl; $R^1$ and $R^2$ represent methyl; and $R^3$ represents hydrogen.

In a ninth preferred embodiment the pyrazolyl-quinazoline derivative of the invention is a compound of Formula I wherein n is 0; X represents NR'; R' together with Y and together with the nitrogen to which they are attached form a pyrrolidinyl or piperidinyl ring; and $R^1$, $R^2$ and $R^3$, independently of each other, represent methyl, ethyl or propyl.

In a tenth preferred embodiment the pyrazolyl-quinazoline derivative of the invention is a compound of Formula I wherein n is 0; X represents NR'; and R' together with Y and together with the nitrogen to which they are attached form a pyrrolidinyl, piperidinyl, piperazinyl or morpholinyl ring; $R^1$ and $R^2$, independently of each other, represent methyl, ethyl or propyl; and $R^3$ represents hydrogen.

In an eleventh preferred embodiment the pyrazolyl-quinazoline derivative of the invention is a compound of Formula I wherein n is 1; and X represents NR'; wherein R' represents hydrogen, methyl, ethyl or propyl; Y represents furanyl, thienyl or phenyl, which phenyl may optionally be substituted one or two times with halo or trifluoromethyl; and $R^1$, $R^2$ and $R^3$, independently of each other, represent methyl, ethyl or propyl.

In a most preferred embodiment the pyrazolyl-quinazoline derivative of the invention is

[2-(3,5-Dimethyl-pyrazol-1-yl)-quinazolin-4-yl]-propylamine;

[2-(3,5-Dimethyl-pyrazol-1-yl)-quinazolin-4-yl]-ethylamine;

[2-(3,5-Dimethyl-pyrazol-1-yl)-quinazolin-4-yl]-diethylamine;

Butyl-[2-(3,5-dimethyl-pyrazol-1-yl)-quinazolin-4-yl]-amine;

Allyl-[2-(3,5-dimethyl-pyrazol-1-yl)-quinazolin-4-yl]-amine;

Cyclopropyl-[2-(3,5-dimethyl-pyrazol-1-yl)-quinazolin-4-yl]-amine;

Cyclopentyl-[2-(3,5-dimethyl-pyrazol-1-yl)-quinazolin-4-yl]-amine;

Cyclohexyl-[2-(3,5-dimethyl-pyrazol-1-yl)-quinazolin-4-yl]-amine;

Cycloheptyl-[2-(3,5-dimethyl-pyrazol-1-yl)-quinazolin-4-yl]-amine;

Cyclooctyl-[2-(3,5-dimethyl-pyrazol-1-yl)-quinazolin-4-yl]-amine;

2-(3,5-Dimethyl-pyrazol-1-yl)-4-piperidin-1-yl-quinazoline;

[2-(3,5-Dimethyl-pyrazol-1-yl)-quinazolin-4-yl]-piperidin-4-yl-amine;

Benzyl-[2-(3,5-dimethyl-pyrazol-1-yl)-quinazolin-4-yl]-amine;

(4-Chloro-benzyl)-[2-(3,5-dimethyl-pyrazol-1-yl)-quinazolin-4-yl]-amine;

(3,4-Difluoro-benzyl)-[2-(3,5-dimethyl-pyrazol-1-yl)-quinazolin-4-yl]-amine;

[2-(3,5-Dimethyl-pyrazol-1-yl)-quinazolin-4-yl]-furan-2-yl-methyl-amine;

[2-(3,5-Dimethyl-pyrazol-1-yl)-quinazolin-4-yl]-thiophen-2-ylmethyl-amine;

[2-(3,5-Dimethyl-pyrazol-1-yl)-quinazolin-4-yl]-phenyl-amine;

(4-Chloro-phenyl)-[2-(3,5-dimethyl-pyrazol-1-yl)-quinazolin-4-yl]-amine;

(3-Chloro-phenyl)-[2-(3,5-dimethyl-pyrazol-1-yl)-quinazolin-4-yl]-amine;

(2-Chloro-phenyl)-[2-(3,5-dimethyl-pyrazol-1-yl)-quinazolin-4-yl]-amine;

(3,4-Dichloro-phenyl)-[2-(3,5-dimethyl-pyrazol-1-yl)-quinazolin-4-yl]-amine;

(4-Bromo-phenyl)-[2-(3,5-dimethyl-pyrazol-1-yl)-quinazolin-4-yl]-amine;

[2-(3,5-Dimethyl-pyrazol-1-yl)-quinazolin-4-yl]-(4-trifluoromethyl-phenyl)-amine;

[2-(3,5-Dimethyl-pyrazol-1-yl)-quinazolin-4-yl]-(3-trifluoromethyl-phenyl)-amine;

[2-(3,5-Dimethyl-pyrazol-1-yl)-quinazolin-4-yl]-(3-methoxy-phenyl)-amine;

[2-(3,5-Dimethyl-pyrazol-1-yl)-quinazolin-4-yl]-p-tolyl-amine;

[2-(3,5-Dimethyl-pyrazol-1-yl)-quinazolin-4-yl]-m-tolyl-amine;
[2-(3,5-Dimethyl-pyrazol-1-yl)-quinazolin-4-yl]-o-tolyl-amine;
[2-(3,5-Dimethyl-pyrazol-1-yl)-quinazolin-4-yl]-naphthalen-2-yl-amine;
[2-(3,5-Dimethyl-pyrazol-1-yl)-quinazolin-4-yl]-(1,2,3,4-tetrahydro-naphthalen-1-yl)-amine;
[2-(3,5-Dimethyl-pyrazol-1-yl)-quinazolin-4-yl]-(2-pyrrolidin-1-yl-ethyl)-amine;
Cyclohexyl-[2-(3-methyl-pyrazol-1-yl)-quinazolin-4-yl]-amine;
S-[2-(3,5-Dimethyl-pyrazol-1-yl)-quinazolin-4-yl]-(S)-1,2,3,4-tetrahydro-naphthalen-1-yl-amine;
[2-(3,5-Dimethyl-pyrazol-1-yl)-quinazolin-4-yl]-(1-ethyl-propyl)-amine;
[2-(3,5-Diisopropyl-pyrazol-1-yl)-quinazolin-4-yl]-(4-methyl-cyclohexyl)-amine;
[2-(3,5-Dimethyl-pyrazol-1-yl)-quinazolin-4-yl]-pyridin-2-yl-amine;
[2-(3,5-Dimethyl-pyrazol-1-yl)-quinazolin-4-yl]-(4-methyl-cyclohexyl)-amine;
(4-tert-Butyl-cyclohexyl)-[2-(3,5-dimethyl-pyrazol-1-yl)-quinazolin-4-yl]-amine;
[2-(3,5-Dimethyl-pyrazol-1-yl)-quinazolin-4-yl]-(tetrahydro-pyran-4-yl)-amine;
Cyclohexyl-[2-(3,5-diisopropyl-pyrazol-1-yl)-quinazolin-4-yl]-amine;
[2-(3,5-Dimethyl-pyrazol-1-yl)-quinazolin-4-yl]-indan-2-yl-amine;
Benzo[1,3]dioxol-5-yl-[2-(3,5-dimethyl-pyrazol-1-yl)-quinazolin-4-yl]-amine;
(3,5-Bis-trifluoromethyl-phenyl)-[2-(3,5-dimethyl-pyrazol-1-yl)-quinazolin-4-yl]-amine;
[2-(3,5-Dimethyl-pyrazol-1-yl)-quinazolin-4-yl]-(4-morpholin-4-yl-phenyl)-amine;
[2-(3,5-Dimethyl-pyrazol-1-yl)-quinazolin-4-yl]-quinolin-8-yl-amine;
[2-(3,5-Dimethyl-pyrazol-1-yl)-quinazolin-4-yl]-(4-iodo-phenyl)-amine;
Biphenyl-4-yl-[2-(3,5-dimethyl-pyrazol-1-yl)-quinazolin-4-yl]-amine;
[2-(3,5-Dimethyl-pyrazol-1-yl)-quinazolin-4-yl]-(1H-indol-7-yl)-amine; or
Cyclohexyl-(2-pyrazol-1-yl-quinazolin-4-yl)-amine;
or a pharmaceutically acceptable salt thereof.

Any combination of two or more of the embodiments described herein is considered within the scope of the present invention.

Definition of Substituents

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Preferred haloalkyl groups of the invention include trihalomethyl, preferably trifluoromethyl.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention a cycloalkyl group designates a cyclic alkyl group, preferably containing of from three to ten carbon atoms ($C_{3-10}$-cycloalkyl), preferably of from three to eight carbon atoms ($C_{3-8}$-cycloalkyl), including cyclopropyl, cyclobutyl, cyclopentyl, cyclohexyl, cycloheptyl and cyclooctyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention a haloalkoxy group designates an alkoxy group as defined herein, which alkoxy group is substituted one or more times with halo. Preferred haloalkoxy groups of the invention include trihalomethoxy, preferably trifluoromethoxy.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono- or poly-cyclic carbocyclic group designates a mono- or polycyclic hydrocarbon group, which group may in particular be an aromatic hydrocarbon group, i.e. a mono- or polycyclic aryl group, or a saturated hydrocarbon group, or a partially saturated hydrocarbon group. Preferred poly-carbocyclic group are the bicyclic carbocyclic groups.

In the context of this invention a monocyclic or polycyclic, carbocyclic group designates a monocyclic or polycyclic hydrocarbon group. Examples of preferred carbocyclic groups of the invention include cycloalkyl, phenyl, naphthyl, indenyl, azulenyl, anthracenyl, and fluorenyl. Most preferred carbocyclic groups of the invention include phenyl, naphthyl and 1,2,3,4-tetrahydro-naphthyl.

In the context of this invention a monocyclic or polycyclic, heterocyclic group designates a mono- or polycyclic group, which group holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6 membered heterocyclic monocyclic groups. Preferred poly-heterocyclic groups of the invention are the bicyclic heterocyclic groups.

Examples of preferred heterocyclic monocyclic groups of the invention include pyrrolidinyl, in particular pyrrolidin-1-yl, pyrrolidin-2-yl, and pyrrolidin-3-yl; piperidinyl, in particular piperidin-1-yl, piperidin-2-yl, piperidin-3-yl and piperidin-4-yl; furanyl, in particular furan-2-yl and furan-3-yl;

thienyl, in particular thien-2-yl and thien-3-yl; and pyrrolyl, in particular pyrrol-1-yl, pyrrol-2-yl and pyrrol-3-yl.

Isomers

It will be appreciated by those skilled in the art that the compounds of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the enantiomeric compounds (including enantiomeric intermediates) is by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "Enantiomers, Racemates, and Resolutions", John Wiley and Sons, New York (1981).

Optical active compounds can also be prepared from optical active starting materials or intermediates.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The chemical compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The chemical compounds of the invention have been subjected to in vitro experiments and found particularly useful as potassium channel modulating agents. More particularly the compounds of the invention are capable of selectively modulating SK1, SK2 and/or SK3 channels.

Therefore, in another aspect, the invention relates to the use of a chemical compound of the invention for the manufacture of medicaments, which medicament may be useful for the treatment or alleviation of a disease or a disorder associated with the activity of potassium channels, in particular SK channels, more particularly SK1, SK2 and/or SK3 channels.

In a preferred embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, urinary incontinence, bladder outflow obstruction, erectile dysfunction, gastrointestinal dysfunction, secretory diarrhoea, ischaemia, cerebral ischaemia, ischaemic heart disease, angina pectoris, coronary heart disease, ataxia, traumatic brain injury, Parkinson's disease, bipolar disorder, psychosis, schizophrenia, anxiety, depression, mood disorders, dementia, memory and attention deficits, Alzheimer's disease, amyotrophic lateral sclerosis (ALS), dysmenorrhea, narcolepsy, Reynaud's disease, intermittent claudication, Sjorgren's syndrome, arrhythmia, hypertension, myotonic muscle dystrophia, spasticity, xerostomi, diabetes type II, hyperinsulinemia, premature labour, baldness, cancer, irritable bowel syndrome, immune suppression, migraine or pain.

In a more preferred embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another preferred embodiment the disease or a disorder associated with the activity of potassium channels is a respiratory disease, in particular asthma, cystic fibrosis, chronic obstructive pulmonary disease (COPD) or rhinorrhea.

In a third preferred embodiment the disease or a disorder associated with the activity of potassium channels is urinary incontinence.

In a fourth preferred embodiment the disease or a disorder associated with the activity of potassium channels is epilepsy, seizures, absence seizures or convulsions.

In a fifth preferred embodiment the disease or a disorder associated with the activity of potassium channels is a respiratory disease, in particular asthma, cystic fibrosis, chronic obstructive pulmonary disease (COPD) or rhinorrhea.

The compounds tested all showed a biological activity in the micromolar and sub-micromolar range, i.e. of from below 1 to above 100 µM. Preferred compounds of the invention show a biological activity determined as described herein in the in the sub-micromolar and micromolar range, i.e. of from below 0.1 to about 10 µM.

Pharmaceutical Compositions

In yet another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the chemical compound of the invention, or a pharmaceutically acceptable salt or derivative thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a compound of the invention.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

Method A

[2-(3,5-Dimethyl-pyrazol-1-yl)-quinazolin-4-yl]-propylamine, Hydrochloride (Compound A1)

2,4-Dichloroquinazoline (600 mg, 3.01 mmol) was dissolved in acetonitrile (10 mL). Propylamine (200 mg, 3.3 mmol) and triethylamine (2.1 mL, 15 mmol) were added. The mixture was stirred at room temperature over-night. Filtration and evaporation of the filtrate gave a yellow solid, which was dissolved in ethyl acetate and washed three times with water. Drying (magnesium sulphate), filtration and evaporation gave (2-chloro-quinazolin-4-yl)-propylamine as a yellow solid.

(2-Chloro-quinazolin-4-yl)-propylamine (450 mg, 2.03 mmol) was dissolved in acetonitrile (7.5 mL) and 3,5-dimethylpyrazole (215 mg, 2.23 mmol) was added. The mixture was heated in a microwave oven at 170° C. for 20 minutes. Filtration gave [2-(3,5-dimethylpyrazol-1-yl)-quinazolin-4-yl]-propylamine, hydrochloride (290 mg, 51%) as a pale red crystalline compound. Mp. 208° C.

The following compounds are prepared in analogy herewith.

[2-(3,5-Dimethyl-pyrazol-1-yl)-quinazolin-4-yl]-ethylamine, Hydrochloride (Compound A2)

Was prepared according to Method A from 2,4-dichloroquinazoline, ethylamine and 3,5-dimethylpyrazole. Mp. 286° C.

[2-(3,5-Dimethyl-pyrazol-1-yl)-quinazolin-4-yl]-diethyl-amine, Hydrochloride (Compound A3)

Was prepared according to Method A from 2,4-dichloroquinazoline, diethylamine and 3,5-dimethylpyrazole. Mp. 156.3° C.

Butyl-[2-(3,5-dimethyl-pyrazol-1-yl)-quinazolin-4-yl]-amine, Hydrochloride (Compound A4)

Was prepared according to Method A from 2,4-dichloroquinazoline, butylamine and 3,5-dimethylpyrazole. Mp. 98.4° C.

Allyl-[2-(3,5-dimethyl-pyrazol-1-yl)-quinazolin-4-yl]-amine, Hydrochloride (Compound A5)

Was prepared according to Method A from 2,4-dichloroquinazoline, allylamine and 3,5-dimethylpyrazole. Mp. 211-212° C.

Cyclopropyl-[2-(3,5-dimethyl-pyrazol-1-yl)-quinazolin-4-yl]-amine, Hydrochloride (Compound A6)

Was prepared according to Method A from 2,4-dichloroquinazoline, cyclopropylamine and 3,5-dimethylpyrazole. Mp. 254° C.

Cyclopentyl-[2-(3,5-dimethyl-pyrazol-1-yl)-quinazolin-4-yl]-amine, Hydrochloride (Compound A7)

Was prepared according to Method A from 2,4-dichloroquinazoline, cyclopentylamine and 3,5-dimethylpyrazole Mp. 263.2° C.

Cyclohexyl-[2-(3,5-dimethyl-pyrazol-1-yl)-quinazolin-4-yl]-amine, Hydrochloride (Compound A8)

Was prepared according to Method A from 2,4-dichloroquinazoline, cyclohexylamine and 3,5-dimethylpyrazole Mp. 137.6-142.7° C.

Cyclopentyl-[2-(3,5-dimethyl-pyrazol-1-yl)-quinazolin-4-yl]-amine, Hydrochloride (Compound A9)

Was prepared according to Method A from 2,4-dichloroquinazoline, cycloheptylamine and 3,5-dimethylpyrazole. Mp. 207° C.

Cyclooctyl-[2-(3,5-dimethyl-pyrazol-1-yl)-quinazolin-4-yl]-amine, Hydrochloride (Compound A10)

Was prepared according to Method A from 2,4-dichloroquinazoline, cyclooctylamine and 3,5-dimethylpyrazole. Mp. 211° C.

2-(3,5-Dimethyl-pyrazol-1-yl)-4-piperidin-1-yl-quinazoline, Hydrochloride (Compound A11)

Was prepared according to Method A from 2,4-dichloroquinazoline, piperidine and 3,5-dimethylpyrazole. Mp. 157° C.

Benzyl-[2-(3,5-dimethyl-pyrazol-1-yl)-quinazolin-4-yl]-amine, Hydrochloride (Compound A12)

Was prepared according to Method A from 2,4-dichloroquinazoline, benzylamine and 3,5-dimethylpyrazole. Mp. 160.2° C.

(4-Chloro-benzyl)-[2-(3,5-dimethyl-pyrazol-1-yl)-quinazolin-4-yl]-amine, Hydrochloride (Compound A13)

Was prepared according to Method A from 2,4-dichloroquinazoline, 4-chlorobenzylamine and 3,5-dimethylpyrazole. LC-ESI-HRMS [M+H]+ 364.1319 Da. Calc. 364.132898 Da.

(3,4-Difluoro-benzyl)-[2-(3,5-dimethyl-pyrazol-1-yl)-quinazolin-4-yl]-amine, Hydrochloride (Compound A14)

Was prepared according to Method A from 2,4-dichloroquinazoline, 3,4-difluorobenzylamine and 3,5-dimethylpyrazole. Mp. 165° C.

[2-(3,5-Dimethyl-pyrazol-1-yl)-quinazolin-4-yl]-(1,2,3,4-tetrahydro-naphthalen-1-yl)-amine, Hydrochloride (Compound A15)

Was prepared according to Method A from 2,4-dichloroquinazoline, 1,2,3,4-tetrahydro-1-naphthylamine and 3,5-dimethylpyrazole. Mp. 221° C.

S-[2-(3,5-Dimethyl-pyrazol-1-yl)-quinazolin-4-yl]-(S)-1,2,3,4-tetrahydro-naphthalen-1-yl-amine, Hydrochloride (Compound A16)

Was prepared according to Method A from 2,4-dichloroquinazoline, S-1,2,3,4-tetrahydro-1-naphthylamine and 3,5-dimethylpyrazole. Mp. 214° C.

Cyclohexyl-[2-(3-methyl-pyrazol-1-yl)-quinazolin-4-yl]-amine, Hydrochloride (Compound A17)

Was prepared according to Method A from 2,4-dichloroquinazoline, cyclohexylamine and 3-methylpyrazole. Mp. 269-274.3° C.

[2-(3,5-Dimethyl-pyrazol-1-yl)-quinazolin-4-yl]-(1-ethyl-propyl)-amine, Hydrochloride (Compound A18)

Was prepared according to Method A from 2,4-dichloroquinazoline, 3-aminopentane and 3,5-dimethylpyrazole. Mp. 96.4° C.

[2-(3,5-Diisopropyl-pyrazol-1-yl)-quinazolin-4-yl]-(4-methyl-cyclohexyl)-amine, Hydrochloride (Compound A19)

Was prepared according to Method A from 2,4-dichloroquinazoline, 4-methylcyclohexylamine and 3,5-diisopropylpyrazole. Mp. 134.6° C.

[2-(3,5-Dimethyl-pyrazol-1-yl)-quinazolin-4-yl]-(4-methyl-cyclohexyl)-amine, Hydrochloride (Compound A20)

Was prepared according to Method A from 2,4-dichloroquinazoline, 4-methylcyclohexylamine and 3,5-dimethylpyrazole. Mp. 80.4-81.6° C.

(4-tert-Butyl-cyclohexyl)-[2-(3,5-dimethyl-pyrazol-1-yl)-quinazolin-4-yl]-amine, Hydrochloride (Compound A21)

Was prepared according to Method A from 2,4-dichloroquinazoline, 4-tert-butylcyclohexylamine and 3,5-dimethylpyrazole. Mp. 253-255° C.

[2-(3,5-Dimethyl-pyrazol-1-yl)-quinazolin-4-yl]-(tetrahydro-pyran-4-yl)-amine, Hydrochloride (Compound A22)

Was prepared according to Method A from 2,4-dichloroquinazoline, 4-aminotetrahydropuran and 3,5-dimethylpyrazole. Mp. 269-272.3° C.

Cyclohexyl-[2-(3,5-diisopropyl-pyrazol-1-yl)-quinazolin-4-yl]-amine, Hydrochloride (Compound A23)

Was prepared according to Method A from 2,4-dichloroquinazoline, cyclohexylamine and 3,5-diisopropylpyrazole with sodium hydride as base instead of triethylamine. Mp. 83.4-85.3° C.

4-Cyclohexylsulfanyl-2-(3,5-dimethyl-pyrazol-1-yl)-quinazoline, Hydrochloride (Compound A24)

Was prepared according to Method A from 2,4-dichloroquinazoline, cyclohexanylthiol and 3,5-dimethylpyrazole with sodium hydride as base instead of triethylamine. Mp. 92.7-94.1° C.

4-Cyclohexyloxy-2-(3,5-dimethyl-pyrazol-1-yl)-quinazoline, Hydrochloride (Compound A25)

Was prepared according to Method A from 2,4-dichloroquinazoline, cyclohexanol and 3,5-dimethylpyrazole. Mp. 152.9-153.5° C.

[2-(3,5-Dimethyl-pyrazol-1-yl)-quinazolin-4-yl]-indan-2-yl-amine, Hydrochloride (Compound A26)

Was prepared according to Method A from 2,4-dichloroquinazoline, 2-aminoindan and 3,5-dimethylpyrazole. Mp. 212-215° C.

Cyclohexyl-(2-pyrazol-1-yl-quinazolin-4-yl)-amine (Compound A27)

Was prepared according to Method A from 2,4-dichloroquinazoline, cyclohexylamine and pyrazole. LC-ESI-HRMS of [M+H]+ shows 294.173 Da. Calc. 294.17187 Da, dev. 3.8 ppm.

Method B

[2-(3,5-Dimethyl-pyrazol-1-yl)-quinazolin-4-yl]-phenyl-amine (Compound B1)

2,4-Dichloroquinazoline (500 mg, 2.5 mmol) was dissolved in acetonitrile (3 mL). Aniline (260 mg, 2.76 mmol) and triethylamine (380 mg, 3.75 mmol) were added. The mixture was shaken in a sealed vial on a sand bath at 60° C. for 12 hours. Filtration and evaporation of the filtrate gave a yellow solid. Column chromatography (ethylacetate:hexane) gave (2-chloro-quinazolin-4-yl)-propylamine (350 mg, 55%).

(2-Chloro-quinazolin-4-yl)-phenyl amine (250 mg, 0.98 mmol) was dissolved in acetonitrile (4 mL) and 3,5-dimethylpyrazole (140 mg, 1.47 mmol) was added. The mixture was heated in a sealed tube at 130° C. for 12 hours. The mixture was concentrated and the residue basified with sodium hydrogencarbonate, extracted with chloroform dried over anhydrous sodium sulfate filtrated and evaporated. The crude product was purified by column chromatography (ethylacetate/hexane) to give [2-(3,5-dimethyl-pyrazol-1-yl)-quinazolin-4-yl]-phenyl-amine (150 mg, 49%). Mp. 262.4-265.3° C.

The following compounds were prepared in analogy herewith:

(4-Chloro-phenyl)-[2-(3,5-dimethyl-pyrazol-1-yl)-quinazolin-4-yl]-amine (Compound B2)

Was prepared according to Method B from 2,4-dichloroquinazoline, 4-chloroaniline and 3,5-dimethylpyrazole. Mp. 209.3-211.2° C.

(3-Chloro-phenyl)-[2-(3,5-dimethyl-pyrazol-1-yl)-quinazolin-4-yl]-amine (Compound B3)

Was prepared according to Method B from 2,4-dichloroquinazoline, 3-chloroaniline and 3,5-dimethylpyrazole. Mp. 259.1-262.4° C.

(2-Chloro-phenyl)-[2-(3,5-dimethyl-pyrazol-1-yl)-quinazolin-4-yl]-amine (Compound B4)

Was prepared according to Method B from 2,4-dichloroquinazoline, 2-chloroaniline and 3,5-dimethylpyrazole. Mp. 210.4-217.1° C.

(3,4-Dichloro-phenyl)-[2-(3,5-dimethyl-pyrazol-1-yl)-quinazolin-4-yl]-amine (Compound B5)

Was prepared according to Method B from 2,4-dichloroquinazoline, 3,4-di-chloroaniline and 3,5-dimethylpyrazole. Mp. 223.9-226.5° C.

(4-Bromo-phenyl)-[2-(3,5-dimethyl-pyrazol-1-yl)-quinazolin-4-yl]-amine (Compound B6)

Was prepared according to Method B from 2,4-dichloroquinazoline, 4-bromoaniline and 3,5-dimethylpyrazole. Mp. 116.2-168.3° C.

[2-(3,5-Dimethyl-pyrazol-1-yl)-quinazolin-4-yl]-(4-trifluoromethyl-phenyl)-amine (Compound B7)

Was prepared according to Method B from 2,4-dichloroquinazoline, 4-trifluoromethylaniline and 3,5-dimethylpyrazole. Mp. 218.8-220.1° C.

[2-(3,5-Dimethyl-pyrazol-1-yl)-quinazolin-4-yl]-(3-methoxy-phenyl)-amine (Compound B8)

Was prepared according to Method B from 2,4-dichloroquinazoline, m-anisidine and 3,5-dimethylpyrazole. Mp. 193.1-194.7° C.

[2-(3,5-Dimethyl-pyrazol-1-yl)-quinazolin-4-yl]-p-tolyl-amine (Compound B9)

Was prepared according to Method B from 2,4-dichloroquinazoline, p-toluidine and 3,5-dimethylpyrazole. Mp. 210.4-216.2° C.

[2-(3,5-Dimethyl-pyrazol-1-yl)-quinazolin-4-yl]-m-tolyl-amine (Compound B10)

Was prepared according to Method B from 2,4-dichloroquinazoline, m-toluidine and 3,5-dimethylpyrazole. Mp. 249.2-250.4° C.

[2-(3,5-Dimethyl-pyrazol-1-yl)-quinazolin-4-yl]-o-tolyl-amine (Compound B11)

Was prepared according to Method B from 2,4-dichloroquinazoline, o-toluidine and 3,5-dimethylpyrazole. Mp. 240.1-244.4° C.

[2-(3,5-Dimethyl-pyrazol-1-yl)-quinazolin-4-yl]-naphthalen-2-yl-amine (Compound B12)

Was prepared according to Method B from 2,4-dichloroquinazoline, 2-naphthylamine and 3,5-dimethylpyrazole. Mp. 213.3-215.6° C.

Benzo[1,3]-dioxol-5-yl-[2-(3,5-dimethyl-pyrazol-1-yl)-quinazolin-4-yl]-amine (Compound B13)

Was prepared according to Method B from 2,4-dichloroquinazoline, 3,4-(methylenedioxy)aniline and 3,5-dimethylpyrazole. LC-ESI-HRMS of [M+H]+ shows 360.148 Da. Calc. 360.14605 Da, dev. 5.4 ppm.

(3,5-Bis-trifluoromethyl-phenyl)-[2-(3,5-dimethyl-pyrazol-1-yl)-quinazolin-4-yl]-amine (Compound B14)

Was prepared according to Method B from 2,4-dichloroquinazoline, 3,5-bis(trifluoromethylmethyl)aniline and 3,5-dimethylpyrazole. Mp. 169.2-172.4° C.

[2-(3,5-Dimethyl-pyrazol-1-yl)-quinazolin-4-yl]-(4-morpholin-4-yl-phenyl)-amine (Compound B15)

Was prepared according to Method B from 2,4-dichloroquinazoline, N-(4-aminophenyl)-morpholine and 3,5-dimethylpyrazole. Mp. 268.2-270.4° C.

[2-(3,5-Dimethyl-pyrazol-1-yl)-quinazolin-4-yl]-quinolin-8-yl-amine (Compound B16)

Was prepared according to Method B from 2,4-dichloroquinazoline, 8-aminoquinoline and 3,5-dimethylpyrazole. Mp. 183.5-184.8° C.

[2-(3,5-Dimethyl-pyrazol-1-yl)-quinazolin-4-yl]-(4-iodo-phenyl)-amine (Compound B17)

Was prepared according to Method B from 2,4-dichloroquinazoline, 4-indoaniline and 3,5-dimethylpyrazole. Mp. 226.5-229.1° C.

Biphenyl-4-yl-[2-(3,5-dimethyl-pyrazol-1-yl)-quinazolin-4-yl]-amine (Compound B18)

Was prepared according to Method B from 2,4-dichloroquinazoline, 4-aminobiphenyl and 3,5-dimethylpyrazole. Mp. 267.5-270.3° C.

[2-(3,5-Dimethyl-pyrazol-1-yl)-quinazolin-4-yl]-(3-trifluoromethyl-phenyl)-amine (Compound B19)

Was prepared according to Method B from 2,4-dichloroquinazoline, 3-trifluoromethylaniline and 3,5-dimethylpyrazole. Mp. 233.1-239.6° C.

[2-(3,5-Dimethyl-pyrazol-1-yl)-quinazolin-4-yl]-pyridin-2-yl-amine (Compound B20)

Was prepared according to Method B from 2,4-dichloroquinazoline, 2-aminopyridine and 3,5-dimethylpyrazole. Mp. 126.1-126.8° C.

[2-(3,5-Dimethyl-pyrazol-1-yl)-quinazolin-4-yl]-(1H-indol-7-yl)-amine, Hydrochloride (Compound B21)

Was prepared according to Method B from 2,4-dichloroquinazoline, 6-aminoindole and 3,5-dimethylpyrazole. Mp. 298.5-303.4° C.

Example 2

Biological Activity

This example demonstrates the biological activity of a compound representative of the invention (Compound A8). The ionic current through small-conductance $Ca^{2+}$-activated $K^+$ channels (SK channels, subtype 3) is recorded using the whole-cell configuration of the patch-clamp technique.

The small-conductance $Ca^{2+}$-activated $K^+$ channel, subtype 3 ($SK_3$) was cloned from human skeletal muscle and stably expressed in HEK293 cells.

Stable Expression of $SK_3$ in HEK293 Cells

Human $SK_3$ (hSK3) was sub-cloned into the expression vector pNS3n, a customized vector derived from pcDNA3 (InVitrogen) to give the plasmid construct pNS3_hSK3. HEK293 tissue culture cells were grown in DMEM (Dulbecco's Modified Eagle Medium) supplemented with 10% FCS (foetal calf serum) at 37° C. in 5% $CO_2$. Cells cultured to 50% confluency in a T25 cell culture flask were transfected with 2.5 µg pNS3_hSK3 using lipofectamino (InVitrogen). Transfected cells were selected in media supplemented with 0.25 mg/ml Zeocin. Single clones were picked and propagated in selection media until sufficient cells for freezing were available. Hereafter the cells were cultured in regular medium without selection agent. Expression of functional hSK3 channels was verified by patch-clamp measurements.

Whole-Cell Recordings

Experiments are carried out on one of several patch-clamp set-ups. Cells plated on coverslips are placed in a 15 µl perfusion chamber (flowrate ~1 ml/min) mounted on a IMT-2 microscope. The microscopes are placed on vibration-free tables in grounded Faraday cages. All experiments are performed at room temperature (20-22° C.). EPC-9 patch-clamp amplifiers (HEKA-electronics, Lambrect, Germany) are connected to Macintosh computers via ITC16 interfaces. Data are stored directly on the hard-disk and analysed by IGOR software (Wavemetrics, Lake Oswega, Oreg., USA).

The whole-cell configuration of the patch-clamp technique is applied. In short: The tip of a borosilicate pipette (resistance 2-4 MΩ) is gently placed on the cell membrane using remote control systems. Light suction results in the formation of a giga seal (pipette resistance increases to more than 1 GΩ) and the cell membrane underneath the pipette is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs—as well as capacitance compensation are updated during the experiments (before each stimulus). All experiments with drifting Rs-values are discharged. Leak-subtractions are not performed.

Solutions

The extracellular (bath) solution contains (in mM): 140 NaCl, 4 KCl, 0.1 $CaCl_2$, 3 $MgCl_2$, 10 HEPES (pH=7.4 with HCl). The test compound was dissolved 1000 times in DMSO from a concentrated stock solution and then diluted in the extracellular solution.

The intracellular (pipette) solution has the following composition (in mM): 105 KCl, 45 KOH, 10 EGTA, 1.21 $MgCl_2$, 7.63 $CaCl_2$, and 10 HEPES (pH=7.2 with HCl). The calculated free concentration of $Ca^{2+}$ in this solution is 300 nM and that of $Mg^{2+}$ is 1 mM.

Quantification

After establishment of the whole-cell configuration, voltage-ramps (normally −120 to +30 mV) are applied to the cell every 5 seconds from a holding potential of −80 mV. A stable baseline current is obtained within a period of 100-500 seconds, and the compound is then added by changing to an extracellular solution containing the test compound. Very little endogenous current (<200 pA at 30 mV compared to 2-10 nA $SK_3$ current) is activated under these circumstances in native HEK293 cells.

Active compounds are quantified by calculating the change in baseline current at −20 mV. The current in the absence of compound is set to 100%. Activators will have values greater than 100, and a value of 200% indicates a doubling of the current. On the other hand, a value of 50% indicates that the compound has reduced the baseline current to half its value.

For activators a $SC_{100}$ value may be estimated. The $SC_{100}$ value is defined as the Stimulating Concentration required for increasing the baseline current by 100%. The $SC_{100}$ value determined for Compound A8 of the invention was 0.035 µM, which is an indication of its strong $SK_3$ activating properties.

The invention claimed is:

1. A pyrazolyl-quinazoline compound of Formula I

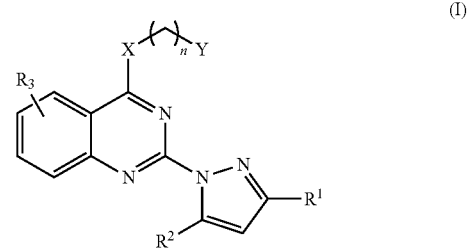

or a pharmaceutically acceptable salt thereof, wherein
n is 0 or 1;
X represents O, S or NR'; wherein
R' represents hydrogen or alkyl;
Y represents alkyl or alkenyl, or a monocyclic or polycyclic, carbocyclic group selected from cycloalkyl, phenyl, naphthyl, 1,2,3,4-tetrahydro-naphthyl and indanyl, or a monocyclic or polycyclic heterocyclic group selected from pyridinyl, indolyl tetrahydropyranyl and guinolinyl, or heterocyclic group, which carbocyclic or heterocyclic groups may optionally be substituted one or more times with substituents selected from the group consisting of alkyl, halo, haloalkyl, alkoxy, methylenedioxy, phenyl and morpholinyl;

or, when n is 0 and X is NR', Y together with R' and together with the nitrogen to which they are attached form a piperidinyl ring; and $R^1$, $R^2$ and $R^3$ independently of each other, represent hydrogen or alkyl.

2. The pyrazolyl-quinazoline compound of claim 1, or a pharmaceutically acceptable salt thereof, wherein n is 0.

3. The pyrazolyl-quinazoline compound of claim 1, or a pharmaceutically acceptable salt thereof, wherein X represents NR'; wherein R' represents hydrogen or alkyl.

4. The pyrazolyl-quinazoline compound of claim 1, or a pharmaceutically acceptable salt thereof, wherein n is 0;

X represents NR'; and

R' together with Y and together with the nitrogen to which they are attached form a piperidinyl ring.

5. The pyrazolyl-quinazoline compound of claim 1, or a pharmaceutically acceptable salt thereof, wherein Y represents alkyl or alkenyl, or a monocyclic or polycyclic, carbocyclic or heterocyclic group, selected from cycloalkyl, phenyl, naphthyl, 1,2,3,4-tetrahydro-naphthyl and indanyl, which carbocyclic groups may optionally be substituted one or more times with substituents selected from the group consisting of alkyl, halo, haloalkyl, alkoxy, methylenedioxy, phenyl and morpholinyl.

6. The pyrazolyl-quinazoline compound of claim 5, or a pharmaceutically acceptable salt thereof, wherein Y represents alkyl, alkenyl or cycloalkyl.

7. The pyrazolyl-quinazoline compound of claim 5, or a pharmaceutically acceptable salt thereof, wherein Y represents a monocyclic or polycyclic carbocyclic group selected from phenyl, naphthyl, 1,2,3,4-tetrahydro-naphthyl and indanyl, which carbocyclic groups may optionally be substituted one or more times with substituents selected from the group consisting of alkyl, halo, haloalkyl, alkoxy, methylenedioxy, phenyl and morpholinyl.

8. The pyrazolyl-quinazoline compound of claim 5, or a pharmaceutically acceptable salt thereof, wherein Y represents a heterocyclic group selected from pyridinyl, indolyl, tetrahydro-pyranyl and quinolinyl.

9. The pyrazolyl-quinazoline compound of claim 1, or a pharmaceutically acceptable salt thereof, wherein $R^1$, $R^2$ and $R^3$ independently of each other, represent hydrogen or alkyl.

10. The pyrazolyl-quinazoline compound of claim 9, or a pharmaceutically acceptable salt thereof, wherein $R^1$ and $R^2$ independently of each other, represent hydrogen or alkyl; and $R^3$ represents hydrogen.

11. The pyrazolyl-quinazoline compound of claim 1, or a pharmaceutically acceptable salt thereof, wherein n is 0;

X represents O, S or NR'; wherein R' represents hydrogen, methyl, ethyl or propyl;

Y represents alkyl, alkenyl, cycloalkyl, alkyl-cycloalkyl; and $R^1$ and $R^2$ represent methyl or isopropyl; and $R^3$ represents hydrogen.

12. The pyrazolyl-quinazoline compound of claim 1, or a pharmaceutically acceptable salt thereof, wherein n is 0 or 1;

X represents NH;

Y represents phenyl, optionally substituted one or two times with substituents selected from the group consisting of alkyl, halo, haloalkyl, alkoxy, methylenedioxy, phenyl and morpholinyl;

$R^1$ and $R^2$ represent methyl or isopropyl; and $R^3$ represents hydrogen.

13. The pyrazolyl-quinazoline compound of claim 1, or a pharmaceutically acceptable salt thereof, wherein n is 0;

X represents NR'; and

R' together with Y and together with the nitrogen to which they are attached form a piperidinyl ring; and $R^1$ and $R^2$, independently of each other, represent methyl, ethyl or propyl; and $R^3$ represents hydrogen.

14. The pyrazolyl-quinazoline compound of claim 1, which is

[2-(3,5-Dimethyl-pyrazol-1-yl)-quinazolin-4-yl]-propylamine;

[2-(3,5-Dimethyl-pyrazol-1-yl)-quinazolin-4-yl]-ethylamine;

[2-(3,5-Dimethyl-pyrazol-1-yl)-quinazolin-4-yl]-diethylamine;

Butyl-[2-(3,5-dimethyl-pyrazol-1-yl)-quinazolin-4-yl]-amine;

Allyl-[2-(3,5-dimethyl-pyrazol-1-yl)-quinazolin-4-yl]-amine;

Cyclopropyl-[2-(3,5-dimethyl-pyrazol-1-yl)-quinazolin-4-yl]-amine;

Cyclopentyl-[2-(3,5-dimethyl-pyrazol-1-yl)-quinazolin-4-yl]-amine;

Cyclohexyl-[2-(3,5-dimethyl-pyrazol-1-yl)-quinazolin-4-yl]-amine;

Cycloheptyl-[2-(3,5-dimethyl-pyrazol-1-yl)-quinazolin-4-yl]-amine;

Cyclooctyl-[2-(3,5-dimethyl-pyrazol-1-yl)-quinazolin-4-yl]-amine;

2-(3,5-Dimethyl-pyrazol-1-yl)-4-piperidin-1-yl-quinazoline;

[2-(3,5-Dimethyl-pyrazol-1-yl)-quinazolin-4-yl]-piperidin-4-yl-amine;

Benzyl-[2-(3,5-dimethyl-pyrazol-1-yl)-quinazolin-4-yl]-amine;

(4-Chloro-benzyl)-[2-(3,5-dimethyl-pyrazol-1-yl)-quinazolin-4-yl]-amine;

(3,4-Difluoro-benzyl)-[2-(3,5-dimethyl-pyrazol-1-yl)-quinazolin-4-yl]-amine;

[2-(3,5-Dimethyl-pyrazol-1-yl)-quinazolin-4-yl]-furan-2-ylmethyl-amine;

[2-(3,5-Dimethyl-pyrazol-1-yl)-quinazolin-4-yl]-thiophen-2-ylmethyl-amine;

[2-(3,5-Dimethyl-pyrazol-1-yl)-quinazolin-4-yl]-phenylamine;

(4-Chloro-phenyl)-[2-(3,5-dimethyl-pyrazol-1-yl)-quinazolin-4-yl]-amine;

(3-Chloro-phenyl)-[2-(3,5-dimethyl-pyrazol-1-yl)-quinazolin-4-yl]-amine;

(2-Chloro-phenyl)-[2-(3,5-dimethyl-pyrazol-1-yl)-quinazolin-4-yl]-amine;

(3,4-Dichloro-phenyl)-[2-(3,5-dimethyl-pyrazol-1-yl)-quinazolin-4-yl]-amine;

(4-Bromo-phenyl)-[2-(3,5-dimethyl-pyrazol-1-yl)-quinazolin-4-yl]-amine;

[2-(3,5-Dimethyl-pyrazol-1-yl)-quinazolin-4-yl]-(4-trifluoromethyl-phenyl)-amine;
[2-(3,5-Dimethyl-pyrazol-1-yl)-quinazolin-4-yl]-(3-trifluoromethyl-phenyl)-amine;
[2-(3,5-Dimethyl-pyrazol-1-yl)-quinazolin-4-yl]-(3-methoxy-phenyl)-amine;
[2-(3,5-Dimethyl-pyrazol-1-yl)-quinazolin-4-yl]-p-tolyl-amine;
[2-(3,5-Dimethyl-pyrazol-1-yl)-quinazolin-4-yl]-m-tolyl-amine;
[2-(3,5-Dimethyl-pyrazol-1-yl)-quinazolin-4-yl]-o-tolyl-amine;
[2-(3,5-Dimethyl-pyrazol-1-yl)-quinazolin-4-yl]-naphthalen-2-yl-amine;
[2-(3,5-Dimethyl-pyrazol-1-yl)-quinazolin-4-yl]-(1,2,3,4-tetrahydro-naphthalen-1-yl)-amine;
[2-(3,5-Dimethyl-pyrazol-1-yl)-quinazolin-4-yl]-(2-pyrrolidin-1-yl-ethyl)-amine;
Cyclohexyl-[2-(3-methyl-pyrazol-1-yl)-quinazolin-4-yl]-amine;
S-[2-(3,5-Dimethyl-pyrazol-1-yl)-quinazolin-4-yl]-(S)-1,2,3,4-tetrahydro-naphthalen-1-yl-amine;
[2-(3,5-Dimethyl-pyrazol-1-yl)-quinazolin-4-yl]-(1-ethyl-propyl)-amine;
[2-(3,5-Diisopropyl-pyrazol-1-yl)-quinazolin-4-yl]-(4-methyl-cyclohexyl)-amine;
[2-(3,5-Dimethyl-pyrazol-1-yl)-quinazolin-4-yl]-pyridin-2-yl-amine;
[2-(3,5-Dimethyl-pyrazol-1-yl)-quinazolin-4-yl]-(4-methyl-cyclohexyl)-amine;
(4-tert-Butyl-cyclohexyl)-[2-(3,5-dimethyl-pyrazol-1-yl)-quinazolin-4-yl]-amine;
[2-(3,5-Dimethyl-pyrazol-1-yl)-quinazolin-4-yl]-(tetrahydro-pyran-4-yl)-amine;
Cyclohexyl-[2-(3,5-diisopropyl-pyrazol-1-yl)-quinazolin-4-yl]-amine;
[2-(3,5-Dimethyl-pyrazol-1-yl)-quinazolin-4-yl]-indan-2-yl-amine;
Benzo[1,3]dioxol-5-yl-[2-(3,5-dimethyl-pyrazol-1-yl)-quinazolin-4-yl]-amine;
(3,5-Bis-trifluoromethyl-phenyl)-[2-(3,5-dimethyl-pyrazol-1-yl)-quinazolin-4-yl]-amine;
[2-(3,5-Dimethyl-pyrazol-1-yl)-quinazolin-4-yl]-(4-morpholin-4-yl-phenyl)-amine;
[2-(3,5-Dimethyl-pyrazol-1-yl)-quinazolin-4-yl]-quinolin-8-yl-amine;
[2-(3,5-Dimethyl-pyrazol-1-yl)-quinazolin-4-yl]-(4-iodophenyl)-amine;
Biphenyl-4-yl-[2-(3,5-dimethyl-pyrazol-1-yl)-quinazolin-4-yl]-amine;
[2-(3,5-Dimethyl-pyrazol-1-yl)-quinazolin-4-yl]-(1H-indol-7-yl)-amine; or
Cyclohexyl-(2-pyrazol-1-yl-quinazolin-4-yl)-amine;
or a pharmaceutically acceptable salt thereof.

15. A pharmaceutical composition comprising a therapeutically effective amount of a pyrazolyl-quinazoline compound according to claim 1, or a pharmaceutically acceptable addition salt thereof, together with at least one pharmaceutically-acceptable carrier or diluent.

\* \* \* \* \*